(12) United States Patent
Ichikawa et al.

(10) Patent No.: US 7,160,239 B2
(45) Date of Patent: Jan. 9, 2007

(54) METHOD OF BREAKING CANCER CELL TISSUE BY MICROELECTROMAGNETIC RADIATION AND MICROELECTROMAGNETIC RADIATOR

(75) Inventors: Masahide Ichikawa, Tokyo (JP); Karou Maeda, Tokyo (JP)

(73) Assignees: Yasuki Takano, Tokyo (JP); Masahide Ichikawa, Tokyo (JP); Karou Maeda, Kanagawa (JP)

( * ) Notice: Subject to any disclaimer, the term of this patent is extended or adjusted under 35 U.S.C. 154(b) by 489 days.

(21) Appl. No.: 10/471,554

(22) PCT Filed: Mar. 12, 2002

(86) PCT No.: PCT/JP02/02296

§ 371 (c)(1),
(2), (4) Date: Sep. 12, 2003

(87) PCT Pub. No.: WO02/072198

PCT Pub. Date: Sep. 19, 2002

(65) Prior Publication Data

US 2004/0097781 A1    May 20, 2004

(30) Foreign Application Priority Data

| Mar. 12, 2001 | (JP) | ............... 2001-116098 |
| Mar. 30, 2001 | (JP) | ............... 2001-136683 |
| May 10, 2001 | (JP) | ............... 2001-177766 |

(51) Int. Cl.
   *A61N 2/00*   (2006.01)

(52) U.S. Cl. ............................................. 600/9
(58) Field of Classification Search ............... 600/9–15
   See application file for complete search history.

(56) References Cited

U.S. PATENT DOCUMENTS

| 4,537,181 | A | * | 8/1985 | Shalhoob et al. | ............... 600/9 |
| 5,090,423 | A | | 2/1992 | Matsuda et al. | |
| 5,270,616 | A | * | 12/1993 | Itatani | .................... 315/111.21 |
| 6,424,864 | B1 | * | 7/2002 | Matsuura | ........................ 607/3 |
| 6,971,983 | B1 | * | 12/2005 | Cancio | ........................ 600/9 |

FOREIGN PATENT DOCUMENTS

| JP | 59-105464 | 6/1984 |
| JP | 1-300964 | 12/1989 |

* cited by examiner

Primary Examiner—John P. Lacyk
(74) Attorney, Agent, or Firm—Wenderoth, Lind & Ponack, L.L.P.

(57) ABSTRACT

A means and apparatus for breaking non-cellular tissues such as cancer cells to be used in medical treatments for human or animal body wherein heat energy is generated due to electric field energy of microelectromagnetic wave radiated from a microelectromagnetic radiator (2) with the use of a magnetron (16) are provided. A cancer cell tissue is radiated with microelectromagnetic wave from the microelectromagnetic radiator (2) composed of the magnetron (16) and an electromagnetic horn (1) and thus active oxygen constituting the cancer cell tissue and electrolytes in the blood acting around the tissue are heated due to the self-vibration by the electrical field energy of the microelectromagnetic wave. Thus, cancer cells are exclusively broken.

2 Claims, 19 Drawing Sheets

Fig. 14
BLOOD TEST
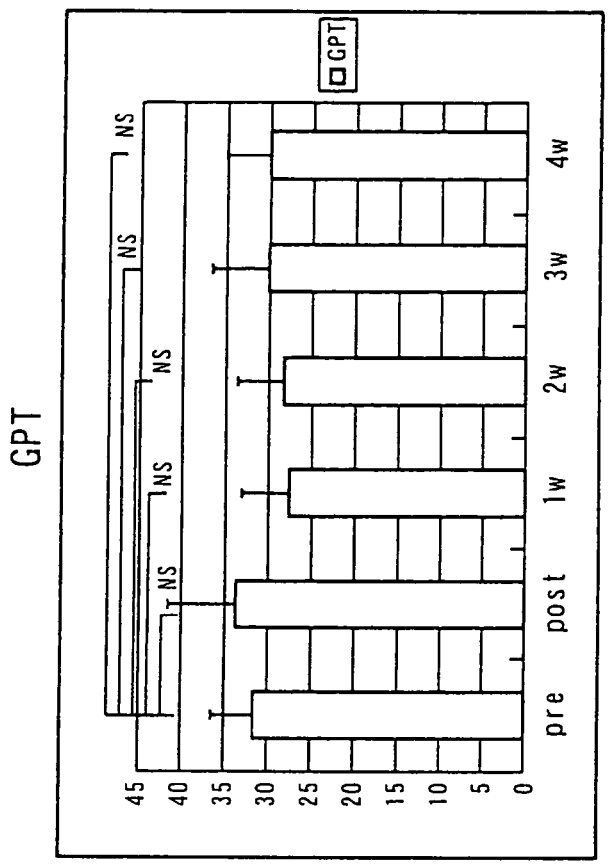
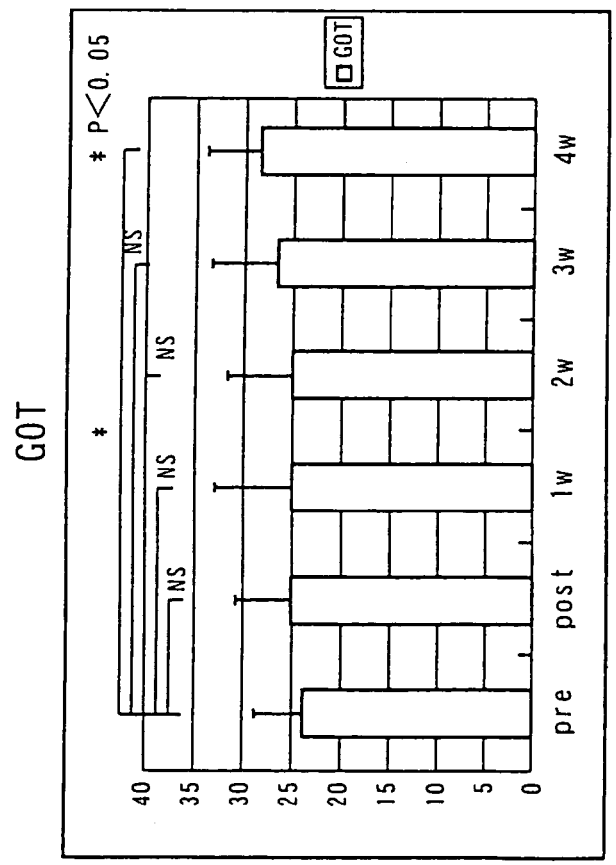

Fig. 15
BLOOD TEST
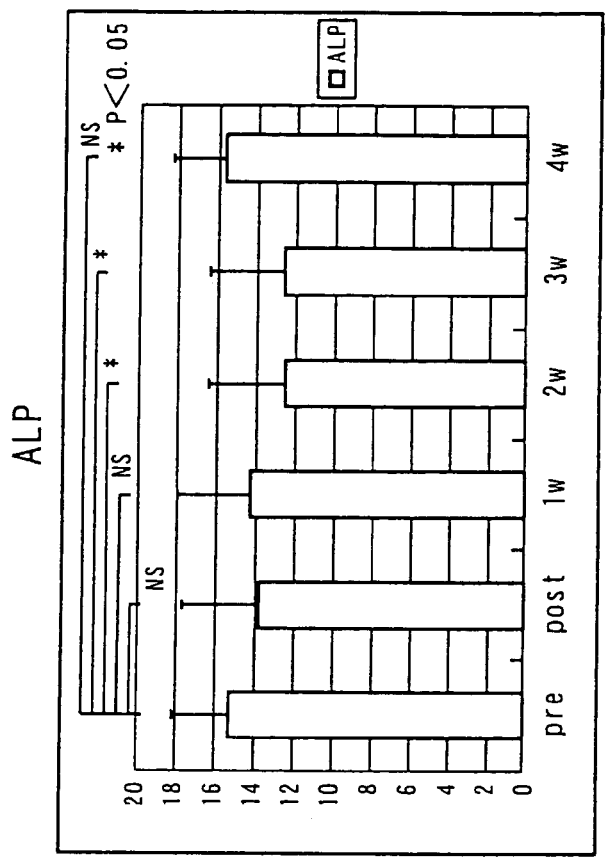
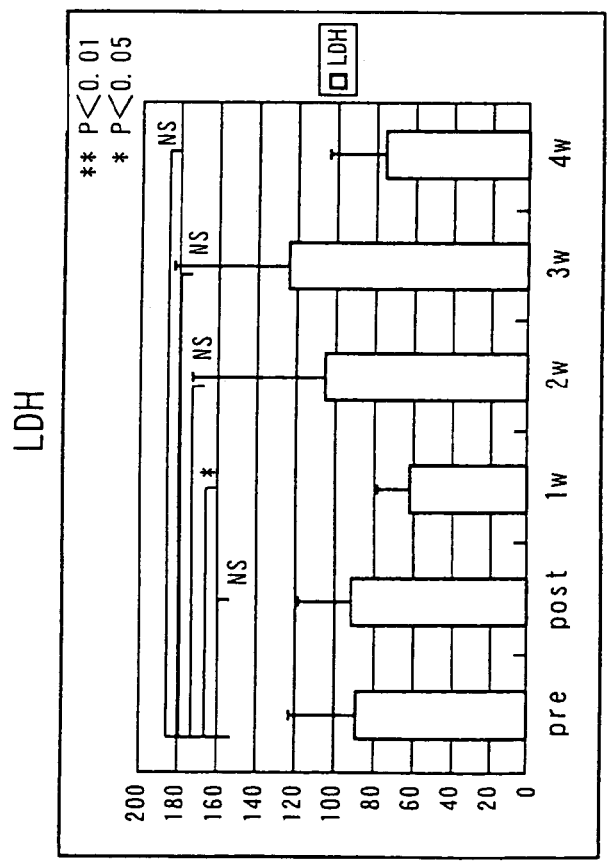

BLOOD TEST
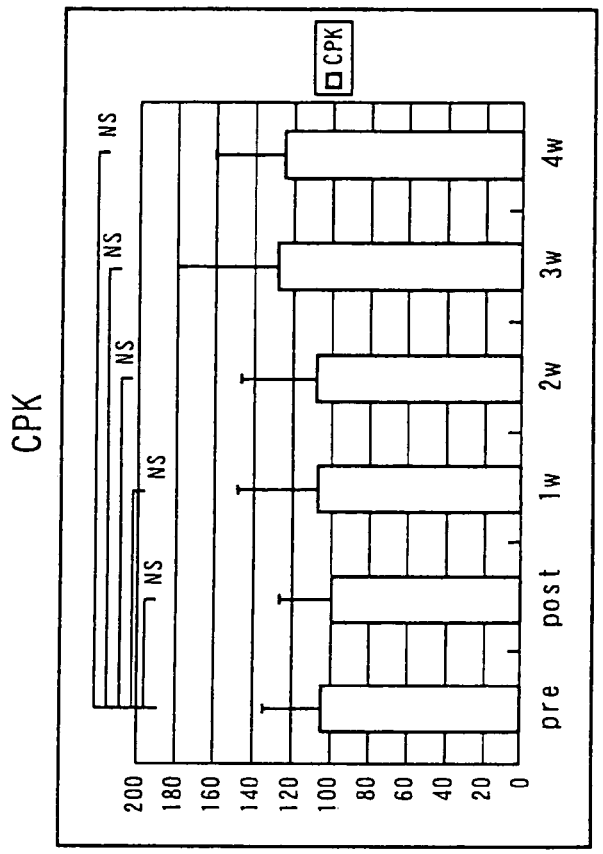
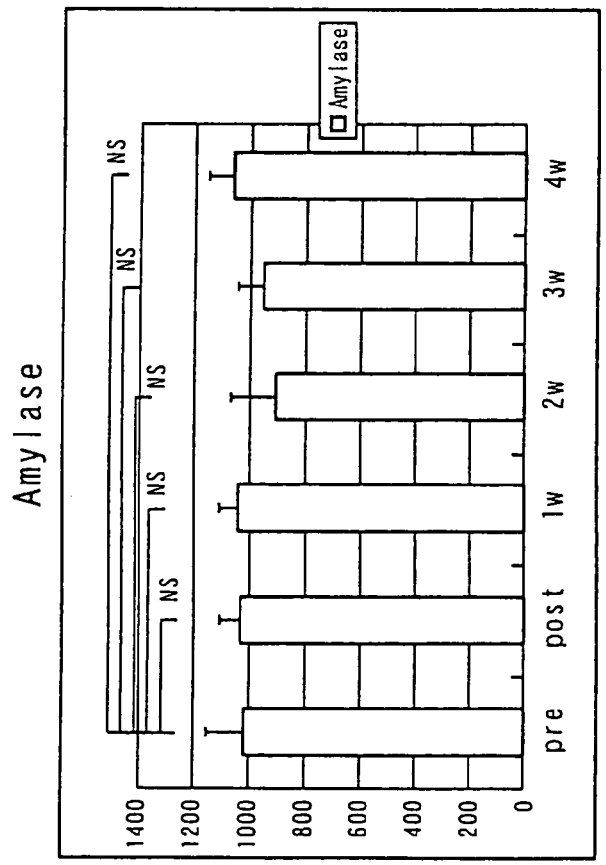
Fig. 16

BLOOD TEST

LIVER FUNCTION
Fig. 18
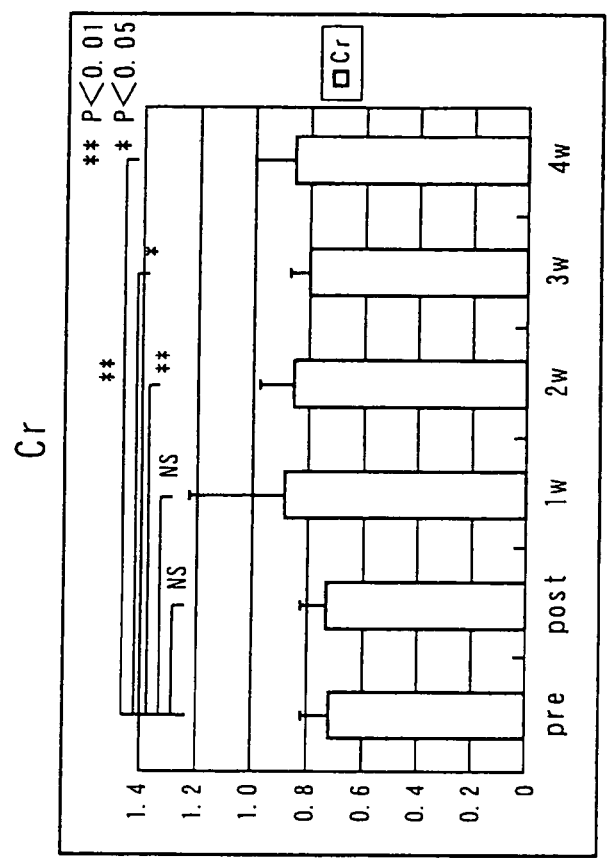
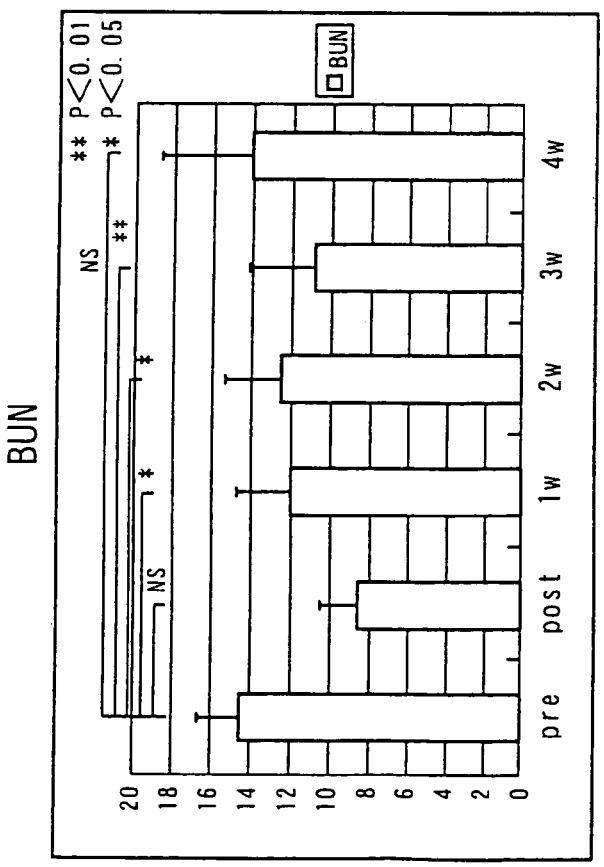

FRACTION OF WHITE CORPUSCLES

METHOD OF BREAKING CANCER CELL TISSUE BY MICROELECTROMAGNETIC RADIATION AND MICROELECTROMAGNETIC RADIATOR

TECHNICAL FIELD

The present invention relates to a method of and an apparatus for giving medical treatment to human bodies and animals, which method and apparatus heat active oxygen and electrolytes by means of the electric field energy of microelectromagnetic waves and break, by means of thermal energy, a cancer cell.

BACKGROUND ART

Various structures for a related art cancer treating medical apparatus provided with a microelectromagnetic radiator exist and are well known. However, there actually exist a multiplicity of structures based on so-called impracticable logic devoid of a clinical test using animals or the like.

A well-known microelectromagnetic radiation therapeutic apparatus which was disclosed in the past as an actually drivable construction is constructed to need a large-sized structure, and also needs a complicated operation and its main construction is merely to radiate electromagnetic waves.

Furthermore, few related arts have referred to the relationship between electromagnetic waves and cancer cells, and there is no related art which has a particularly detailed explanation about the idea of breaking cancer cells by means of electromagnetic waves.

There is not at all a paper on research for breaking hepatitis C and hepatitis B, each of which is caused by a virus which is part of a noncellular tissue, a cancer cell and others, and there has not yet been clinical information on clinical tests using human bodies or experiments using animals or the like, nor is there even an armchair theory.

Incidentally, there presently exists a microelectromagnetic radiation therapeutic apparatus having a construction similar to that of an existing electromagnetic radiation therapeutic apparatus, and a microelectromagnetic radiation therapeutic apparatus of the type explained as that for thermatology is well known.

All of these related arts are only based on an idea which is no better than the concept of physiotherapy, and their structures are generally such that microelectromagnetic waves from a microelectromagnetic radiator are passed through an electrical path such as a coaxial cable, an electrical wire or a cavity duct, to radiate electromagnetic energy. The structures, therefore, need very large-scale devices and operations.

In general, a cancer cell originate in an epithelial tissue, and called an epithelia cancer such as stomach cancer, uterine cancer, lung cancer, breast cancer, liver cancer, esophageal cancer or rectal cancer. Comparing the epithelial tissue with a padded kimono by way of example, the outside of the padded kimono corresponds to the outer layer of skin and the inside corresponds to the mucosa of the skin.

The inside includes the viscera and the organs of a human being and is protected with mucus in a thick state so that the inside mucosa does not dry like the outside skin. A tumor originating in a glandula from which the mucus is secreted is adenocarcinoma, and a tumor originating in the middle of the padded kimono is a malignant tumor which becomes sarcoma.

Hemangiosarcoma, myosarcoma, osteosarcoma, liposarcoma and the like are also widely known. In addition, there are leukemia, malignant lymphoma, encephaloma and like.

An anaplastic carcinoma formed by a cancer which has just primitively originated is a vicious cancer such as a cancer differentiated in an unclear state, and seems to be best suited to treatment using microelectromagnetic waves.

Incidentally, cytological grade values are used in diagnosis of cancer. Diagnosis is performed in accordance with the grading of (1), (2), (3), (4) and (5). These grade values represent: (2) normal; (3) grade at which progress observation is necessary; (4) cancer cell with a 90% probability; and (5) cancer cell with a 100% probability.

On the other hand, in therapeutic fields for eradicating cancer cells, operation, hormonotherapy, chemotherapy, immunotherapy and the like are making progress, but the use of carcinostatics is accompanied by side effects. According to past examples, it has been reported that there is a case where a uterine cancer became a rectal cancer immediately after radiation therapy has been performed on the uterine cancer. However, the effectiveness of these radiation and carcinostatics is also recognized. In addition, there are immunotheraphy free of side effects, herbal medicines and moxibustion, but their therapeutic effects are not yet confirmed.

A university of the United States has recently reported an successful example in which microelectromagnetic waves are used for breast cancer.

Incidentally, it is reported as a clinical example that a cancer cell originates when active oxygen originating in a body adversely affects a cell therein.

The invention has been made by noting these active oxygen and electrolytes, and makes it possible to radiate microelectromagnetic waves (electromagnetic energy: approximately 500 W) from a microelectromagnetic radiator toward a cancer cell of a cancer patient.

Specifically, as shown in FIG. 6, a very large quantity of active oxygen ($O_2^-$) exists in a portion which surrounds a cancer cell, and this radical active oxygen and electrolytes 40 are minus components. Therefore, if the electric fields of microelectromagnetic waves are varied by AC components of + and −, the electric fields of + and − act to cause vibrations 42 of the radical active oxygen, and the radical active oxygen is self-heated and formed into thermal energy 41, so that its temperature rises to 42° C. or higher.

Thus, the cancer cell are broken.

Of course, the electrolytes 40 such as blood existing in the surrounding portion also similarly rise in temperature, and a synergistic effect occurs. It is well known in the medical world that cancer cells are irresistible to heat, and it is natural that cancer cells are broken to death.

In general, an infrared therapeutic device is considerably effective in breaking a cancer cell existing on the surface of a human body, but the electromagnetic waves of far infrared rays are too short in wavelength to reach and break a cancer cell, if the cancer cell or the cellular tissue or the like is in a deep part of the human body. In contrast, microelectromagnetic waves (1.0–5 GHz) can enter the inside of the human body to a satisfactory extent.

Accordingly, if these microelectromagnetic waves are radiated onto a portion surrounding a cancer cell tissue, all portions containing rich electrolytes of minus active oxygen and blood undergo a synergistic effect of heating, and cancer cells or the like except normal cells can be easily broken by their self-heating actions.

DISCLOSURE OF INVENTION

To solve the above-described problem, the invention provides the following construction.

(1) A cancer cell tissue breaking method using microelectromagnetic waves is characterized by: radiating microelectromagnetic waves from a microelectromagnetic radiator made of a magnetron and an electromagnetic horn; and self-vibrating and heating active oxygen which is part of a cancer cell tissue as well as electrolytes such as blood acting in a portion surrounding the cancer cell tissue by means of electric field energy of the microelectromagnetic waves to break only a cancer cell.

(2) A microelectromagnetic radiator apparatus is characterized in that a plurality of microelectromagnetic radiators each including a magnetron and an electromagnetic wave horn are respectively disposed on opposite sides of a body in a mutually opposed manner, the microelectromagnetic radiator apparatus being constructed to radiate microelectromagnetic waves from the respective microelectromagnetic radiators disposed in the mutually opposed manner to cause the microelectromagnetic waves to reach a deep portion of the body.

(3) A microelectromagnetic radiator apparatus as in (2) or (3) is characterized by being constructed to radiate the microelectromagnetic waves from the microelectromagnetic radiators disposed in the mutually opposed manner while rotating the microelectromagnetic radiators or the body.

BRIEF DESCRIPTION OF DRAWINGS

FIG. 3 is a side view schematically showing the microelectromagnetic radiator according to the invention and an explanatory view showing the arrangement of switches and the like;

FIG. 14 shows the result of the experiment, representing in graphic form GOT and GPT of the beagles used for the experiment;

FIG. 15 shows the result of the experiment, representing in graphic form LDH and ALP of the beagles used for the experiment;

FIG. 16 shows the result of the experiment, representing in graphic form the amylase and CPK of the beagles used for the experiment;

FIG. 18 shows the result of the experiment, representing in graphic form BUN and Cr of the beagles used for the experiment;

BEST MODE FOR CARRYING OUT THE INVENTION

Figure 1:
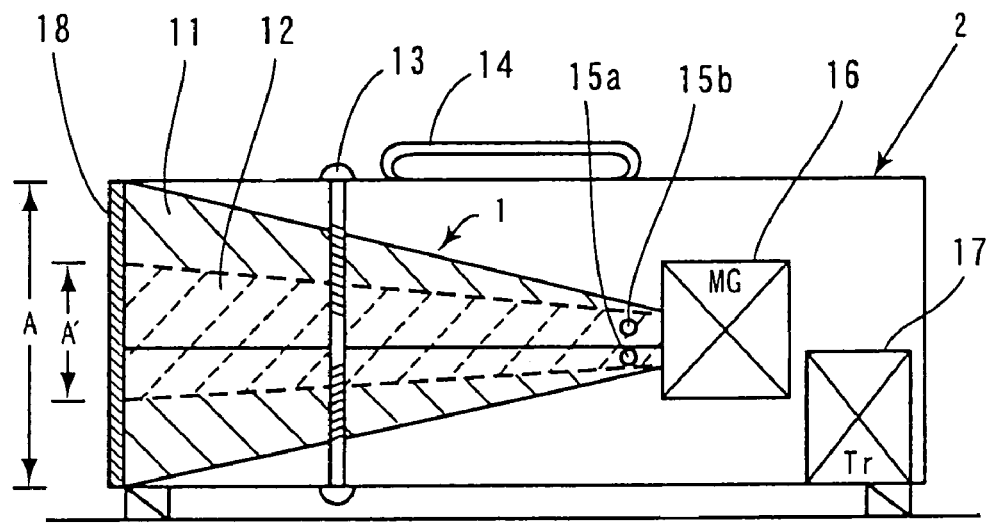
FIG. 1 is a side view schematically showing a microelectromagnetic radiator according to the invention.
Figure 2:
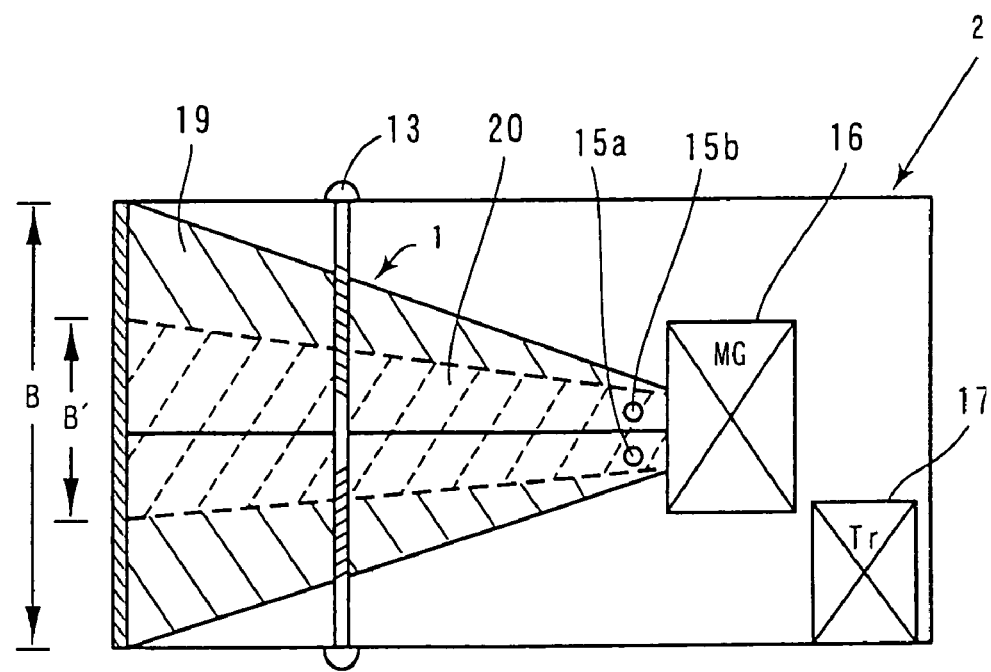
FIG. 2 is a top plan view schematically showing the microelectromagnetic radiator according to the invention.
Figure 3:
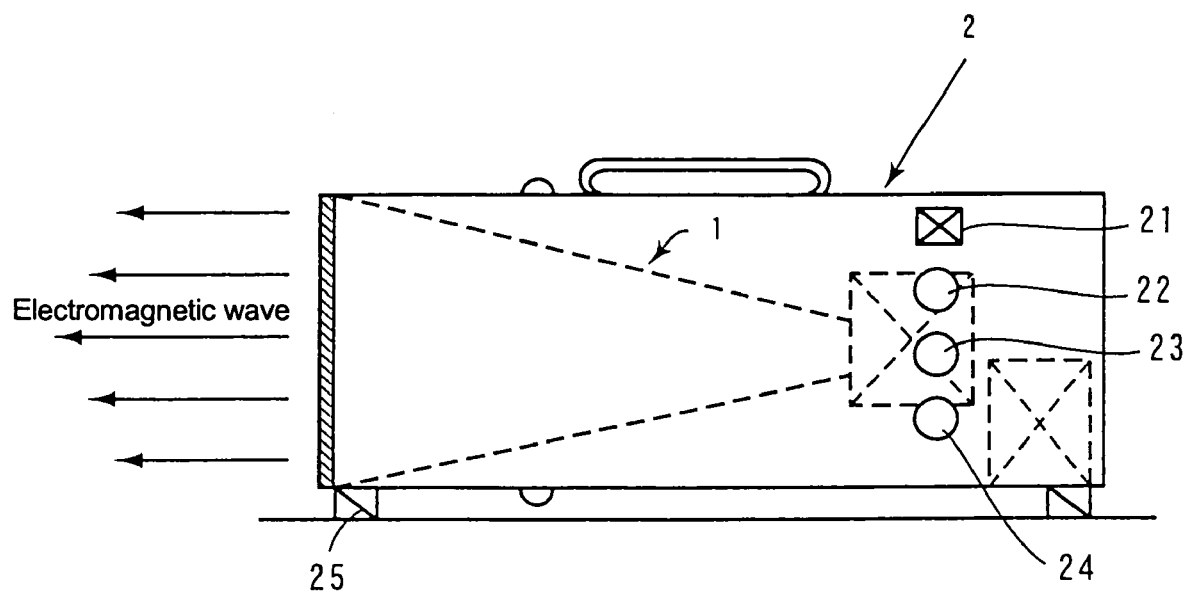
Figure 4:
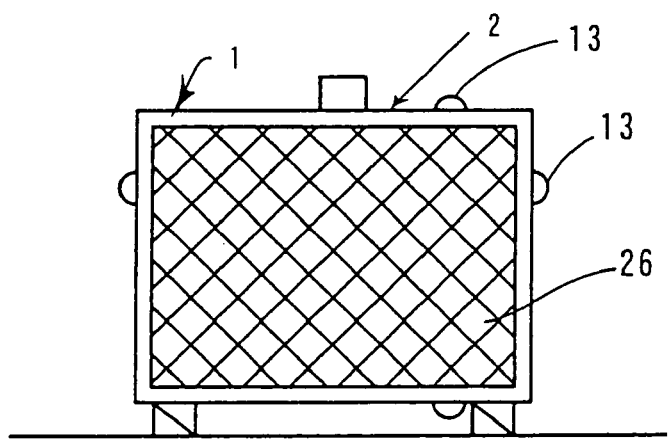
FIG. 4 is an explanatory view showing a front portion of the microelectromagnetic radiator according to the invention.

A method of breaking a cancer cell tissue by means of microelectromagnetic radiation according to the invention and embodiments of a microelectromagnetic radiator apparatus will be described below with reference to the accompanying drawings.

A microelectromagnetic radiator for embodying a method of breaking a cancer cell tissue by means of microelectromagnetic radiator according to the invention generally needs a high voltage of about 4 kVK, and includes a magnetron and electromagnetic radiation in an integrated arrangement and has a variable aperture adjustment radiator part. The microelectromagnetic radiator has a structure in which an electromagnetic horn part of a radiator is movably provided with a partial aperture and is adjusted by means of a mechanical handle or the like.

In general, related-art microelectromagnetic radiators pass their generated microwaves through coaxial cable wires or cavity ducts and radiate electromagnetic energy with extremely large losses. In addition, operators are forced to perform large-scale operations and are placed in extremely dangerous states. Since all such related-art microelectromagnetic radiators have aperture parts of the fixed type, energy radiation planes are fixed, and separate devices are needed for varying the aperture parts.

Since the invention is a microelectromagnetic radiator having a variable aperture adjustment horn having an integrated structure, it is possible to provide a superior microelectromagnetic radiator which is safe and can be reduced in size in terms of its external appearance.

A microelectromagnetic radiator 2 according to a first embodiment includes a magnetron 16 which is supplied with electrical power from a power source transformer 17 and generates microelectromagnetic waves, and an electromagnetic wave horn part 1 made of variable aperture adjustment horn parts 11 and 12, in the form of an integrated structure as shown in FIGS. 1 to 4. Each of the variable aperture adjustment horn parts 11 and 12 has a structure in which longitudinal and lateral variations are given through gears such as moving gears with use of a knob 13 to cause the variable aperture adjustment horn parts 11 and 12 to swing about rotating shafts 15a and 15b so that an aperture part (A–A'·B–B') can be determined according to the constitution of patients to be treated.

The entire frame of a front 18 of the aperture part is covered with an insulative cover 26 in a form which does not scare a patient to be treated, thereby realizing a construction which allows for uneasiness.

Furthermore, the reason why the aperture part is easily adjustable in the moving system of the invention is that it is particularly important to match the space radiation electrical impedance of microelectromagnetic waves, and the maximum condition is that electromagnetic impedance is also made equal according to the constitution of the patient.

The best treatment effect is obtained when the following conditions are satisfied:

microelectromagnetic radiator (internal impedance)=radiation electrical impedance of horn+internal resistance of body.

In addition, if the electromagnetic wave radiating opening of the aperture part A–A'·B–B' is extremely narrow, microelectromagnetic waves suffer an oscillation stop, resulting in an unstable oscillating operation.

As for the control of electrical power, a start switch (22) is turned on, and an indicator lamp 21 of the electrical power is lit. Driving is performed for only the time set by a timer switch (23). In the case of emergency, a stop switch (24) is depressed to shut off the electrical power.

Figure 5:
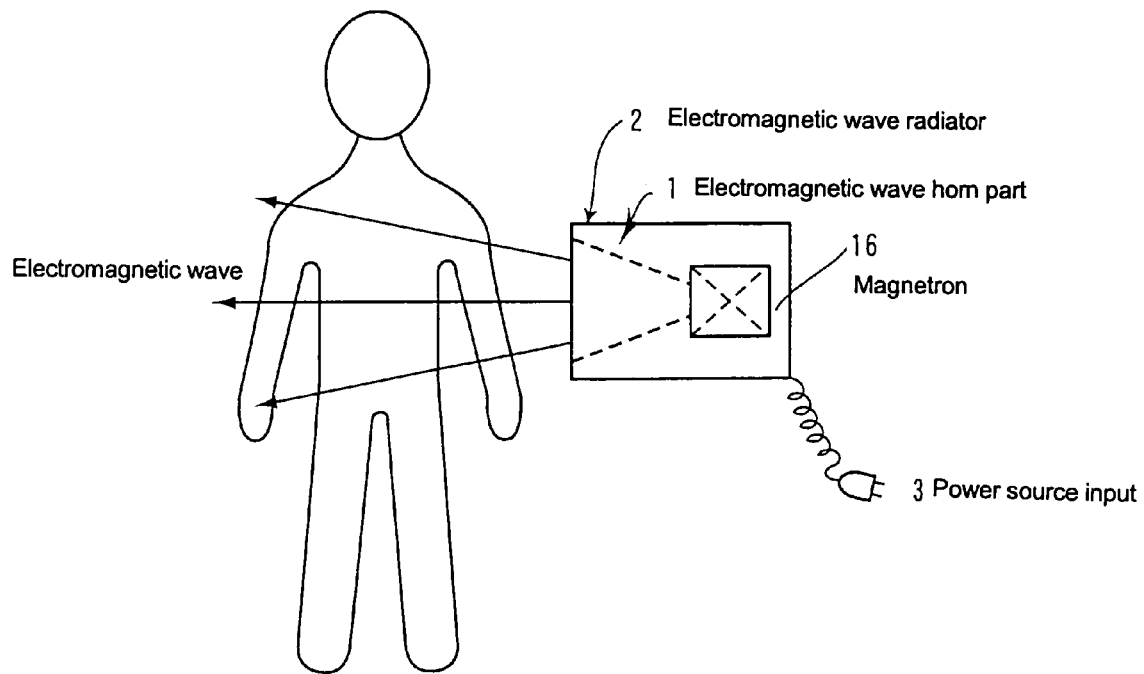
FIG. 5 is an explanatory view showing the case when a body is irradiated with microelectromagnetic waves by using the microelectromagnetic radiator.
Figure 6:
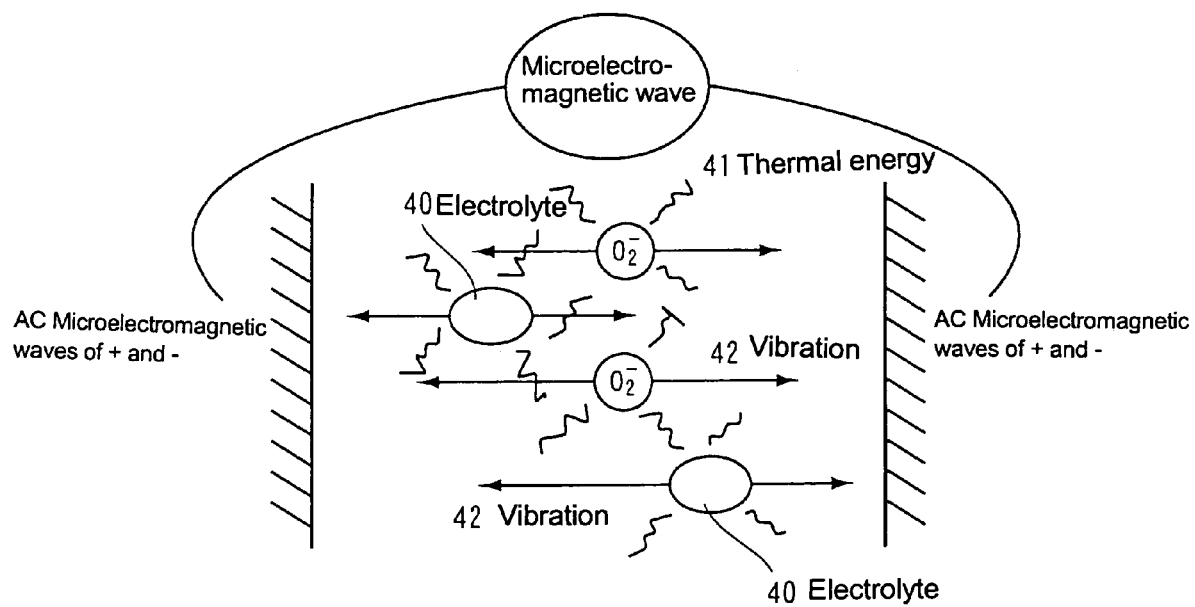
FIG. 6 is an explanatory view showing influences which occur when the electric field of microelectromagnetic waves acts on active oxygen and electrolytes of + and −.

In this manner, as shown in FIG. 5, the apparatus which includes the magnetron 16 and the electromagnetic horn part 1 in the form of the integrated structure radiates microelectromagnetic waves (1.0–5 GHz) with the front of the aperture part directed toward a portion surrounding a cancer cell of a human body or an animal. The electrical power is inserted through a power source input 3 from a household socket.

It is particularly important to match the space radiation electrical impedance of electromagnetic waves, and the maximum condition is that electromagnetic impedance is also made equal according to the constitution of a patient. Therefore, the best effect is obtained when the electromagnetic wave radiating opening is formed in the shape of a horn, and as described above, it is necessary to take the relationship of "microelectromagnetic radiator (internal impedance)=radiation electrical impedance of horn+internal resistance of body".

In clinical test examples using the apparatus of the invention, the effect of treatment on cancer cells occurring in human bodies and animals is remarkably high, but side effects are not at all observed. The data shown in Tables 1, 2 and 3 are enumerated as reference examples.

TABLE 1

Dog Named "Ryoko" Mastadenoma

| | | pre | 6 hrs | 24 hrs | 1 wk |
|---|---|---|---|---|---|
| Kind | | Papillon | | | |
| Sex | | Female | | | |
| Weight | | 1.93 | 1.92 | 1.92 | 1.98 |
| Age | | 8 months | | | |
| General Blood Test | | | | | |
| WBC | /µl | 9150 | 9650 | 9800 | 10500 |
| RBC | ×10$^4$/µl | 714 | 698 | 712 | 715 |
| HB | g/dl | 17.4 | 16.8 | 16.9 | 17.2 |
| HT | % | 44.7 | 48.8 | 44.3 | 47.9 |
| MCV | fl | 63 | 70 | 62 | 67 |
| MCH | pg | 24.4 | 24.1 | 23.7 | 24.1 |
| MCHC | % | 38.9 | 34.1 | 38.1 | 35.9 |
| PLT | ×10$^4$/µl | 28.4 | 39.1 | 35.2 | 44.7 |
| Blood Smear Image | | | | | |
| St | | 0 | 0 | 0 | 0 |
| Seg | | 4758 | 5597 | 5096 | 6090 |
| Lym | | 2654 | 3778 | 3332 | 3045 |
| Mon | | 1007 | 386 | 1078 | 840 |
| Eos | | 732 | 290 | 294 | 525 |
| Others | | 0 | 0 | 0 | 0 |
| Blood Biochemical Test | | 6.0 | 6.6 | 6.0 | 6.4 |
| Total Protein | | | | | |
| Protein Fraction | | | | | |
| GOT | u/l | 32 | 28 | 30 | 68 |
| GPT | u/l | 35 | 34 | 32 | 32 |
| ALP | u/l | 144 | 133 | 133 | 167 |
| TBIL | mg/dl | 0.4 | 0.2 | 0.4 | 0.3 |
| NH3 | µg/dl | 24 | 61 | 347 | 68 |
| LDH | u/l | 56 | 28 | | 53 |
| CPK | u/l | 120 | 83 | 106 | 175 |
| γ-GTP | u/l | 13 | 11 | 7 | 7 |
| GLU | mg/dl | 88 | 93 | 89 | 79 |
| TCHOL | mg/dl | 150 | 170 | 153 | 191 |
| CA-P | mg/dl | 9.5 | 9.2 | 9.5 | 10.2 |
| BUN | mg/dl | 14.5 | 13.8 | 17.6 | 20.6 |
| CREA | mg/dl | 0.6 | 0.6 | 0.5 | 0.5 |
| NA | mEq/l | 147 | 148 | 148 | 148 |
| K | mEq/l | 4.2 | 4.1 | 4.1 | 4.4 |
| CL | mEq/l | 108 | 110 | 111 | 109 |
| Urinalysis | CRP | 0 | | | |
| PH | | 6 | 6 | 6 | 5 |
| Prot | | ± | – | ± | – |
| Glu | | – | – | – | – |
| ket | | – | – | – | – |
| BIL | | – | – | – | – |
| OB | | – | – | – | – |
| Urob | | – | – | – | – |
| Specific Gravity of Urine | | 1.024 | 1.025 | 1.045 | 1.047 |
| Urine Deposit | | Fat Drop + Epithelial Cell + Bacteria +/± Residue | Epithelial Cell + Residue + | Epithelial Cell + Residue + | Epithelial Cell Residue |
| Urine Culture | | — | | | |

TABLE 2

Dog Named "Chatsubo"

| | | pre | 6 hrs | 24 hrs | 1 wk |
|---|---|---|---|---|---|
| Kind | | Pomeranian | | | |
| Sex | | Male | | | |
| Weight | | 4.12 | 3.86 | | 4.02 |
| Age | | 11 months | | | |

TABLE 2-continued

Dog Named "Chatsubo"

| | | pre | 6 hrs | 24 hrs | 1 wk |
|---|---|---|---|---|---|
| General Blood Test | | | | | |
| WBC | /μl | | 17950 | 13950 | 16250 |
| RBC | ×10⁴/μl | | 703 | 778 | 740 |
| HB | g/dl | | 17.0 | 19.0 | 17.7 |
| HT | % | | 46.7 | 49.8 | 47.3 |
| MCV | fl | | 66 | 64 | 64 |
| MCH | pg | | 24.2 | 24.4 | 23.9 |
| MCHC | % | | 36.4 | 38.2 | 37.4 |
| PLT | ×10⁴/μl | | 36.2 | 23.6 | 36.2 |
| Blood Smear Image | | | | | |
| St | | | 0 | 0 | 0 |
| Seg | | | 11847 | 8649 | 9100 |
| Lym | | | 4308 | 3209 | 5038 |
| Mon | | | 898 | 1814 | 813 |
| Eos | | | 898 | 279 | 1300 |
| Others | | | 0 | 0 | 0 |
| Blood Biochemical Test | | | 6.0 | 7.6 | 6.4 |
| Total Protein | | | | | |
| Protein Fraction | | | | | |
| GOT | u/l | | 27 | 41 | 37 |
| GPT | u/l | | 90 | 164 | 95 |
| ALP | u/l | | 268 | 219 | 235 |
| TBIL | mg/dl | | 0.1 | 0.2 | 0.2 |
| NH3 | μg/dl | | | 84 | 83 |
| LDH | u/l | | | 61 | 59 |
| CPK | u/l | | | 127 | 210 |
| γ-GTP | u/l | | 4 | 5 | 4 |
| GLU | mg/dl | | | 126 | 115 |
| TCHOL | mg/dl | | 172 | 247 | 203 |
| CA-P | mg/dl | | 10.6 | 12.1 | 11.3 |
| BUN | mg/dl | | 16 | 20.4 | 32.7 |
| CREA | mg/dl | | 0.8 | 0.8 | 0.8 |
| NA | mEq/l | | 151 | 149 | 149 |
| K | mEq/l | | 4.1 | 3.9 | 3.6 |
| CL | mEq/l | | 113 | 110 | 108 |
| Urinalysis (with Uretheral Catheter) | | | | | |
| PH | | | 7 | 6 | 6 |
| Prot | | | + | ± | + |
| Glu | | | − | − | − |
| ket | | | − | − | − |
| BIL | | | − | − | − |
| OB | | | + | − | − |
| Urob | | | − | − | − |
| Specific Gravity of Urine | | | 1.060 | 1.060 | 1.060 |
| Urine Deposit | | | Epithelial Cell + Struvite Crystal + | White Corpuscle + Epithelial Cell + Struvite Crystal + | Fat Drop + Epithelial Cell + |
| Urine Culture | | | | | |

TABLE 3

Dog Named "Lady" Mastadenoma

| | | pre | 6 hrs | 24 hrs | 1 wk |
|---|---|---|---|---|---|
| Kind | | Cavalier | | | |
| Sex | | Female | | | |

TABLE 3-continued

Dog Named "Lady" Mastadenoma

| | | pre | 6 hrs | 24 hrs | 1 wk |
|---|---|---|---|---|---|
| Weight | | 9.06 | 8.82 | 8.94 | |
| Age | | 3 | | | |
| General Blood Test | | | | | |
| WBC | /μl | | 9950 | 10850 | 9750 |
| RBC | ×10⁴/μl | | 611 | 602 | 603 |
| HB | g/dl | | 17.1 | 15.2 | 15.3 |
| HT | % | | 45.5 | 46.4 | 42.1 |
| MCV | fl | | 74 | 77 | 70 |
| MCH | pg | | 28.0 | 25.2 | 25.4 |
| MCHC | % | | 37.6 | 32.8 | 36.3 |
| PLT | ×10⁴/μl | | 23.0 | 21.0 | 34.2 |
| Blood Smear Image | | | | | |
| St | | | 0 | 0 | 0 |
| Seg | | | 4577 | 5859 | 4875 |
| Lym | | | 3582 | 2713 | 3120 |
| Mon | | | 796 | 1085 | 1073 |
| Eos | | | 995 | 1194 | 683 |
| Others | | | 0 | 0 | 0 |
| Blood Biochemical Test | | | 6.8 | 6.2 | 6.8 |
| Total Protein | | | | | |
| Protein Fraction | | | | | |
| GOT | u/l | | 22 | 25 | 26 |
| GPT | u/l | | 22 | 26 | 28 |
| ALP | u/l | | 85 | 76 | 70 |
| TBIL | mg/dl | | 0.3 | 0.2 | 0.2 |
| NH3 | μg/dl | | 30 | 63 | 104 |
| LDH | u/l | | 75 | 34 | |
| CPK | u/l | | 90 | 79 | 115 |
| γ-GTP | u/l | | 8 | 4 | 5 |
| GLU | mg/dl | | 104 | 99 | 81 |
| TCHOL | mg/dl | | 191 | 171 | 182 |
| CA-P | mg/dl | | 11.0 | 11.2 | 11.0 |
| BUN | mg/dl | | 20.3 | 13.1 | 10.1 |
| CREA | mg/dl | | 0.7 | 0.7 | 0.6 |
| NA | mEq/l | | 148 | 148 | 146 |
| K | mEq/l | | 4.1 | 3.8 | 4.1 |
| CL | mEq/l | | 109 | 108 | 107 |
| Urinalysis | CRP | 0.0 | | | |
| PH | | | 6–7 | 6–7 | 6 |
| Prot | | | + | ± | ± |
| Glu | | | − | − | − |
| ket | | | − | − | − |
| BIL | | | − | − | − |
| OB | | | −/± | − | − |
| Urob | | | − | − | − |
| Specific Gravity of Urine | | | 1.045 | 1.055 | 1.055 |
| Urine Deposit | | | | | |
| Urine Culture | | | | | |

Then, a microelectromagnetic radiator apparatus according to a second embodiment of the invention will be described below.

The invention resides in the fact that a plurality of microelectromagnetic radiators are used, and they are movably disposed around a human body in opposition to one another and their positions can be freely easily adjusted by remote control.

Figure 7:
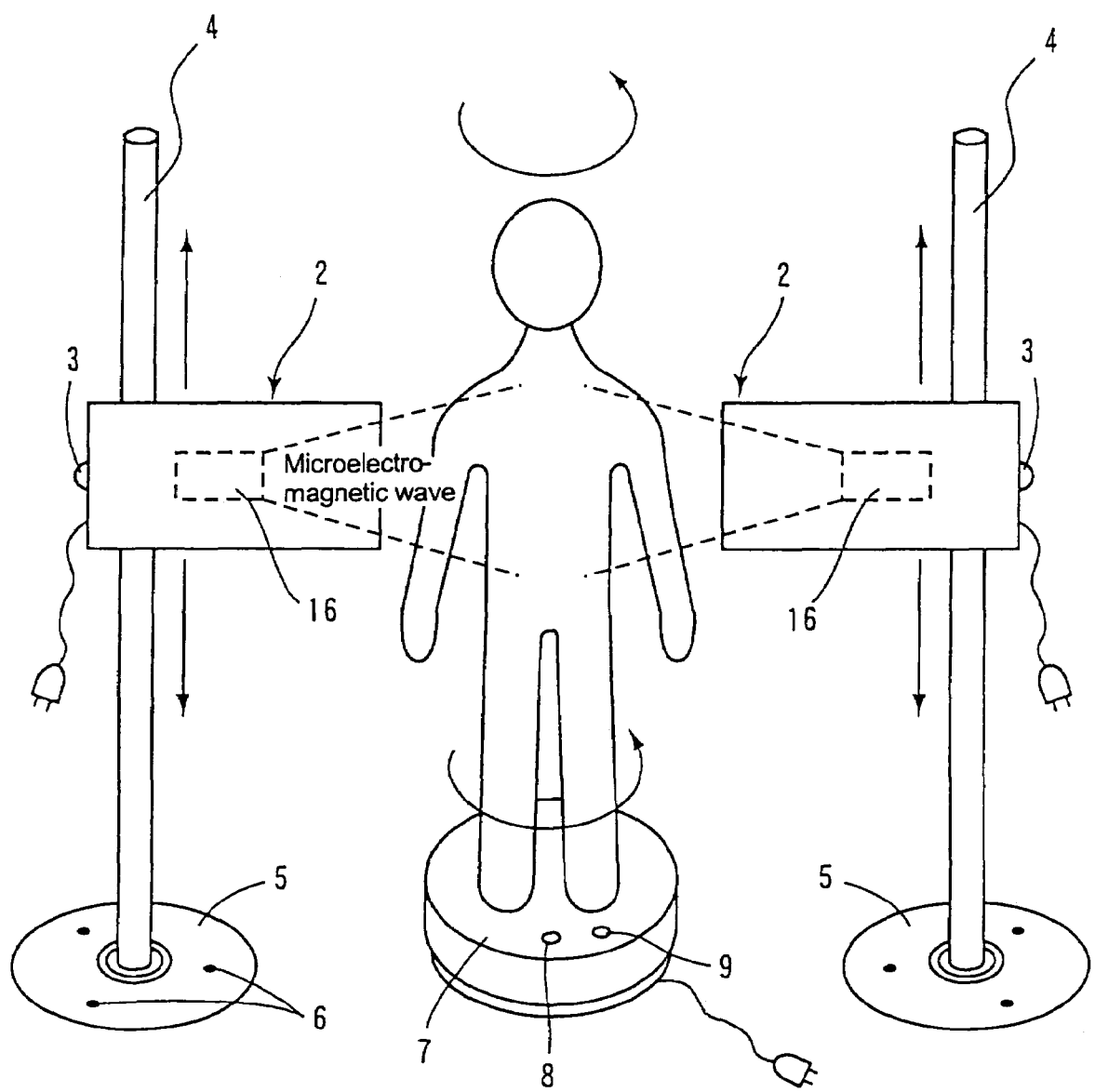
FIG. 7 is an explanatory view showing the manner in which a plurality of microelectromagnetic radiators are oppositely disposed and a body on a rotating base is irradiated with microwaves from sides of the body.

The construction of the apparatus is such that microelectromagnetic radiators 2 are respectively fitted to vertical poles 4 and are fixed with fixing knobs 3 placed in pressure contact with the respective poles 4, as shown in FIG. 7. Otherwise, the microelectromagnetic radiators 2 are constantly held in a free state without being placed in pressure contact so as to facilitate remote control.

When these radiators are to be disposed in plural numbers, they are disposed so that mutually opposed radiation energies are emphasized.

A patient to be treated stands upright on a rotatable base 7 in the middle between the opposed radiators. Otherwise, a base on which a patient is to sit is controlled by a rotation start switch 8 and a rotatable base speed adjusting knob 9.

The patient to be treated is made to stand upright on the base which rotates about a rotating shaft, and the microelectromagnetic radiators 2 are positionally adjusted with respect to an affected part of the body of the patient by longitudinal remote control so that microelectromagnetic waves are easily radiated onto any affected part. Reference numeral 5 denotes a base which fixes the vertical pole to a floor.

In case a patient is not in a serious condition and has a fine cancer cell, the invention needs only to use not a plurality of moving systems but a single moving system, and microelectromagnetic wave radiation from only one side is sufficient.

A basic research on a noninvasive high-power microwave apparatus (microelectromagnetic radiator) for cancer, which is capable of actually breaking a cancer cell or the like by using the microelectromagnetic radiators according to the above-described first and second embodiments will be described below.

Regarding New Microwave Treatment

A presently conducted method is, generally, to transdermally stick a needle up to a position near a focal part of a liver cancer of small area or transurethrally insert an instrument up to an affected part of prostatomegaly, so that weak microwaves are irradiated from the tip to break a cancer tissue by heat. This method is applicable to only tumors limited in size and number, and is no better than symptomatic treatment.

Free radicals which do not exist in normal cells exist in cancer cells. An epoch-making small-sized microwave apparatus (the microelectromagnetic radiators described in the first and second embodiments) has been originally developed on the basis of the theory that when a cancer is irradiated with such a strong microwave, free radicals repeat vibrations at very high speeds for a short time and generate high heat, so that only cancer cells can be selectively broken. In this microwave apparatus, microwaves are irradiated from the outside of a body in a planar form instead of a related-art pinpoint form, to break cancer of wide area and metastatic lesions at a time, and in addition, irradiation time can- be set in units of several seconds. Accordingly, the microwave apparatus aims to minimize the influence of electromagnetic waves. To examine the applicability of this epoch-making noninvasive high-power microwave radiator apparatus to medical fields relative to cancer, various basic experiments were conducted. The results will be presented below.

Embodiments

Experiment 1: Safety Test with Experiments Using Animals

Ten 9- to 11-month-old beagles (of weight 10.9±0.91 kg) were used, and two microwave radiator apparatus (microelectromagnetic radiators) were oppositely disposed at an interval of 60 cm, and each of the experimental animals was made to lie down in the middle between the two microwave radiator apparatus, and microwaves from both apparatus were simultaneously irradiated twice from the forward and rearward directions and twice from the transversal directions at intervals of 2 seconds with an irradiation time of 3 seconds so that not only the liver but also the chest and abdomen of each of the experimental animals could be exposed by one cycle of irradiation. Furthermore, this operation was continuously performed for 3 days in a similar manner, and a health-condition check, a blood test and the like were performed before irradiation, after irradiation, after one week, after two weeks, after three weeks and after four weeks.

(1) Items of Health-Condition Check

Figure 8:
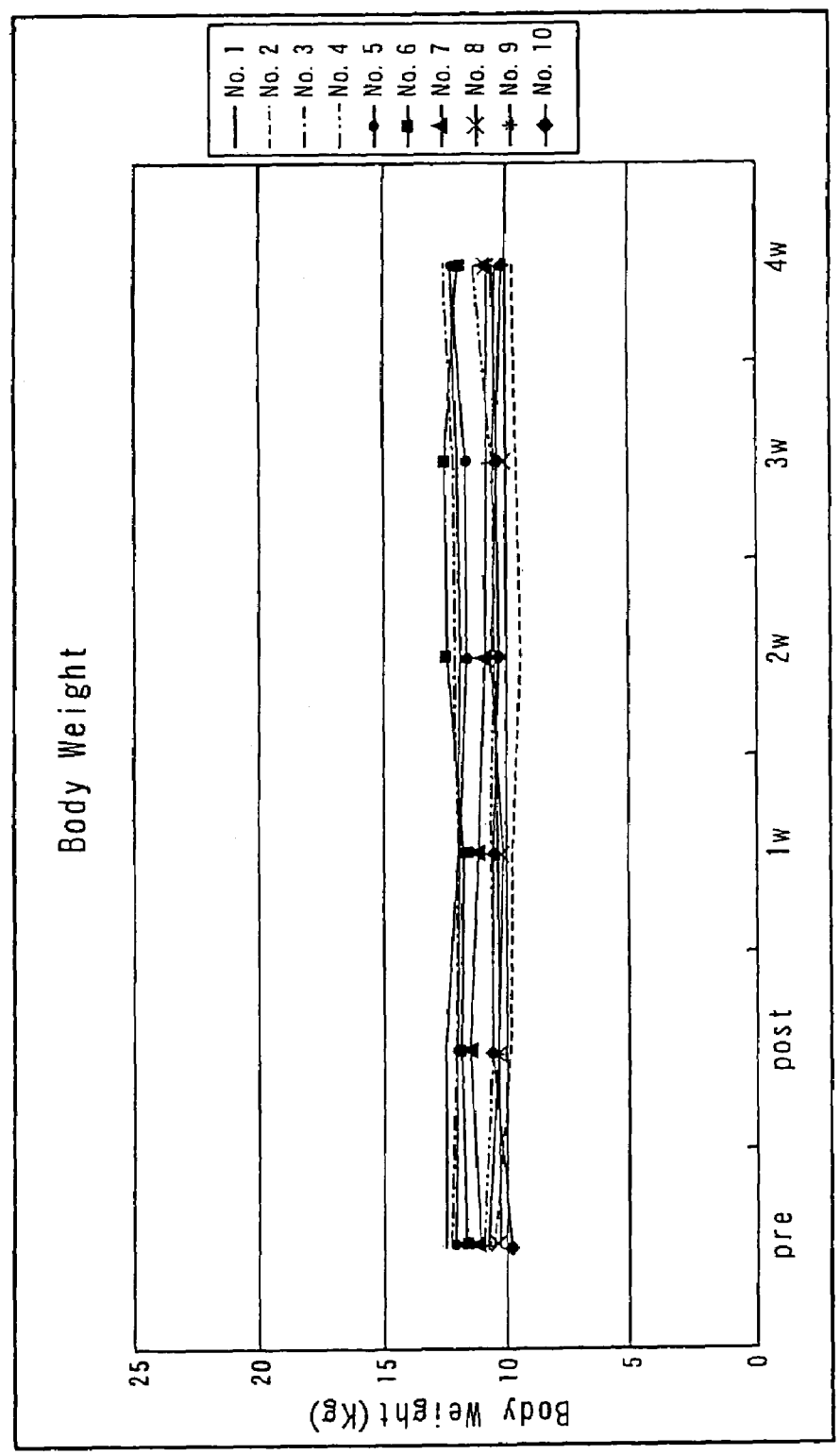
FIG. 8 shows the result of an experiment, representing in graphic form the weights of beagles used for the experiment.
Figure 9:
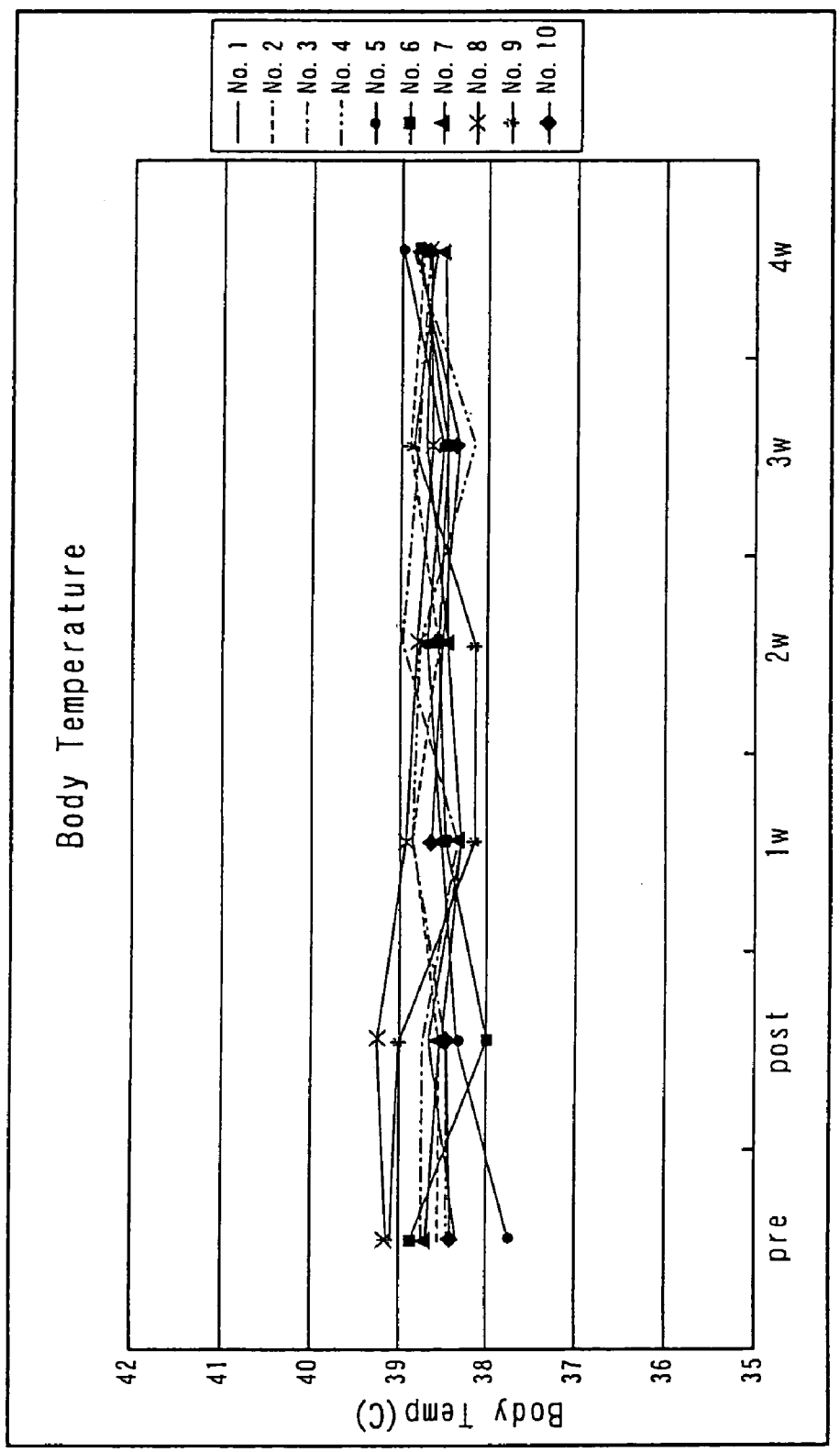
FIG. 9 shows the result of the experiment, representing in graphic form the body temperatures of the beagles used for the experiment.
Figure 10:
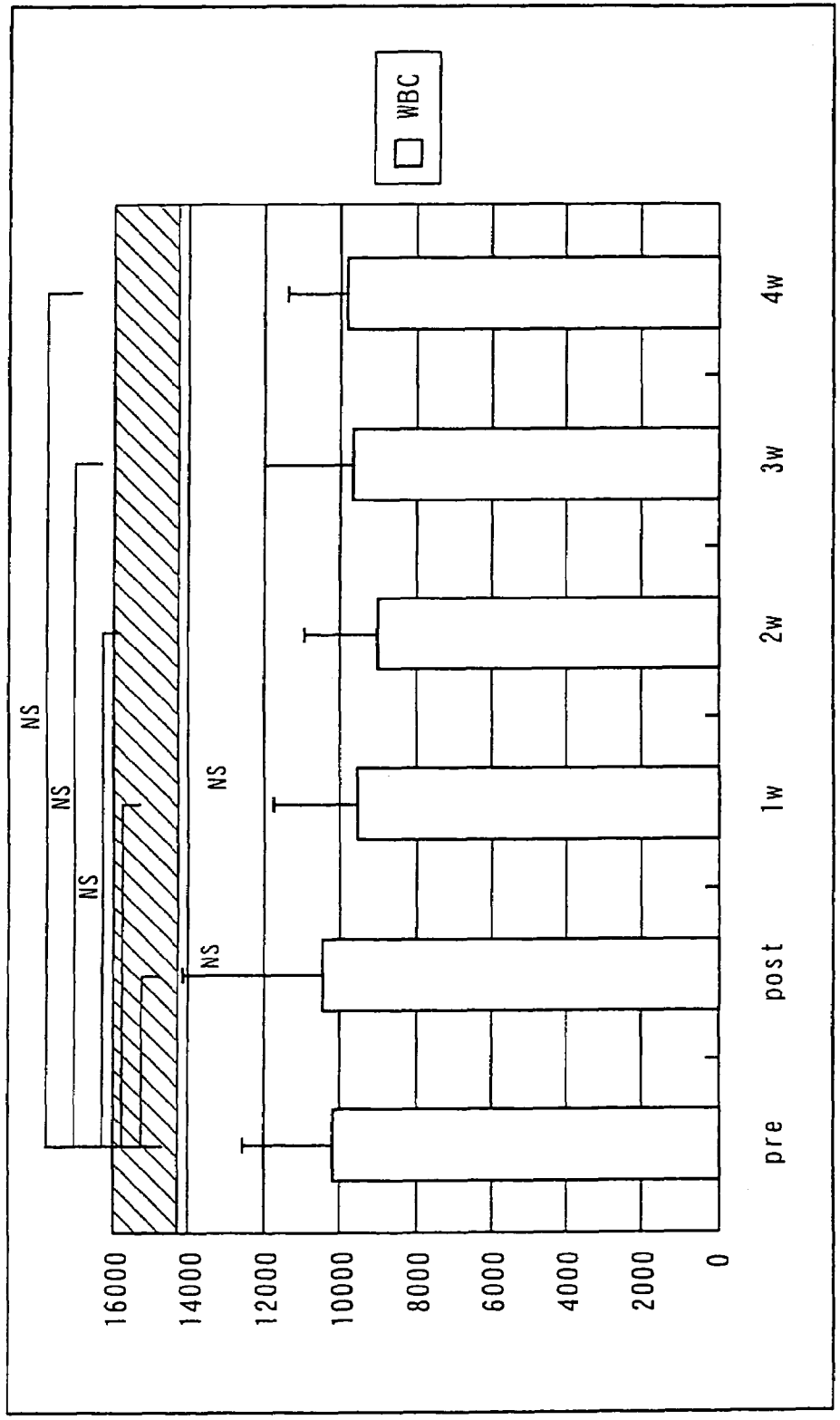
FIG. 10 shows the result of the experiment, representing in graphic form white corpuscles of the beagles used for the experiment.
Figure 11:
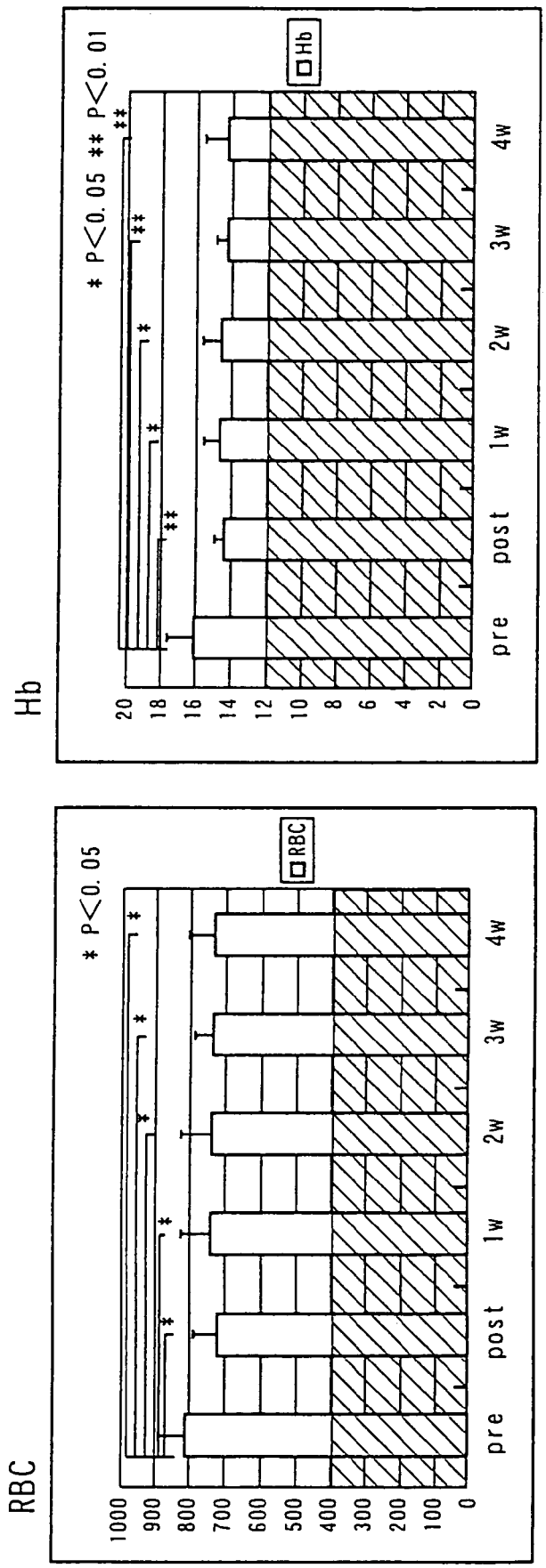
FIG. 11 shows the result of the experiment, representing in graphic form the red corpuscles and the hemoglobin of the beagles used for the experiment.
Figure 12:
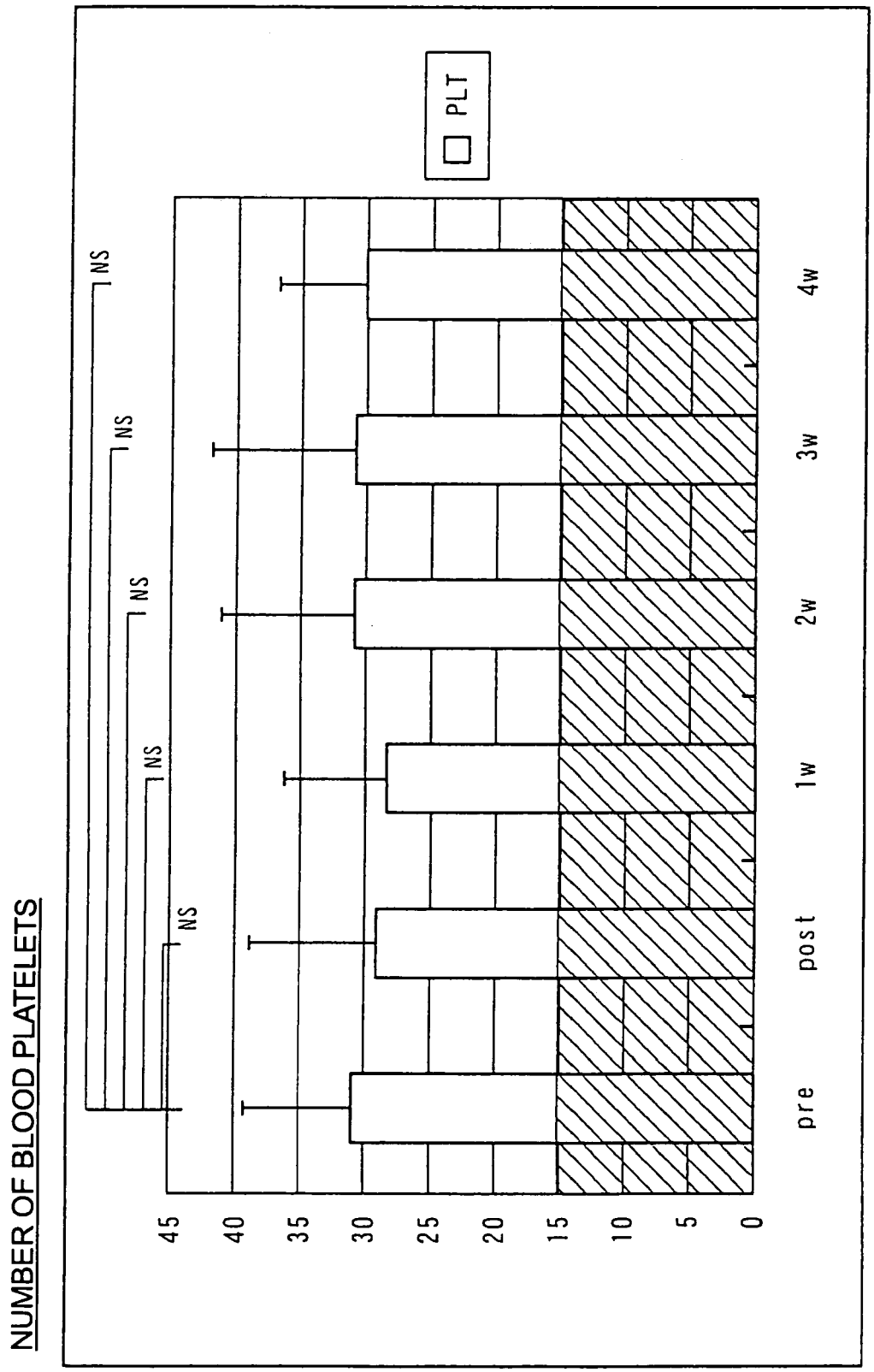
FIG. 12 shows the result of the experiment, representing in graphic form the number of blood platelets of the beagles used for the experiment.
Figure 13:
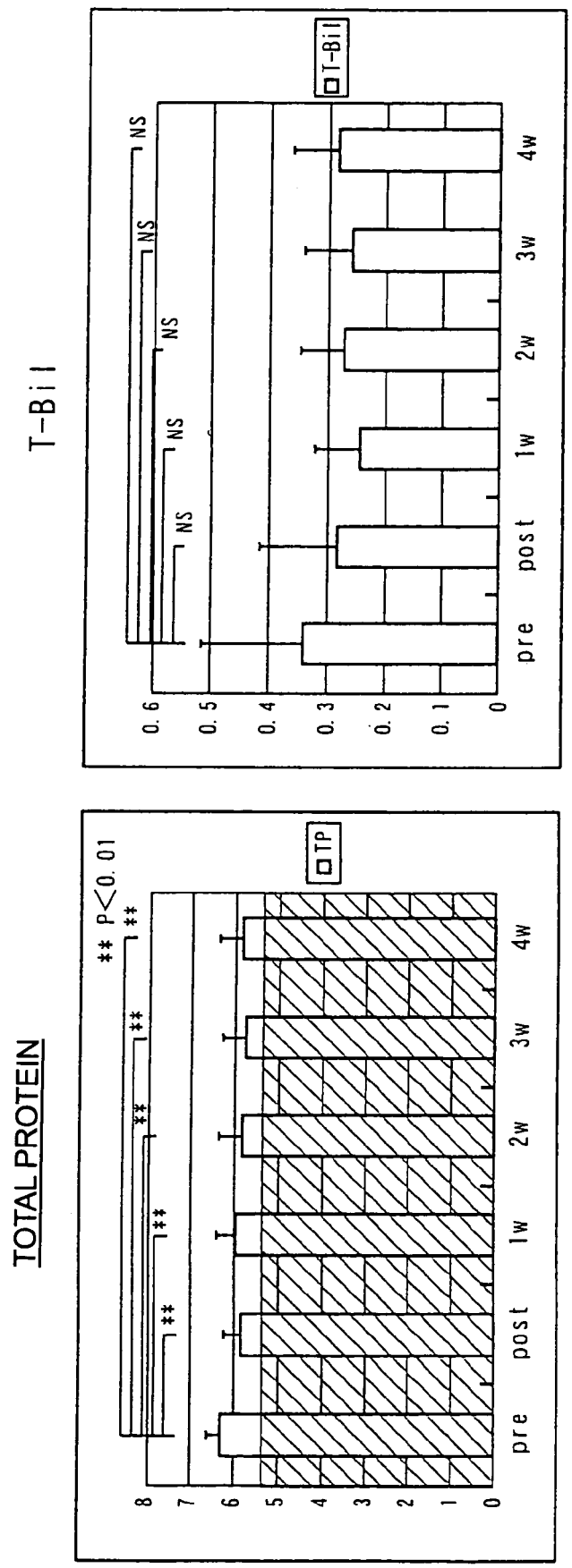
FIG. 13 shows the result of the experiment, representing in graphic form the total protein and T-BiL of the beagles used for the experiment.
Figure 17:
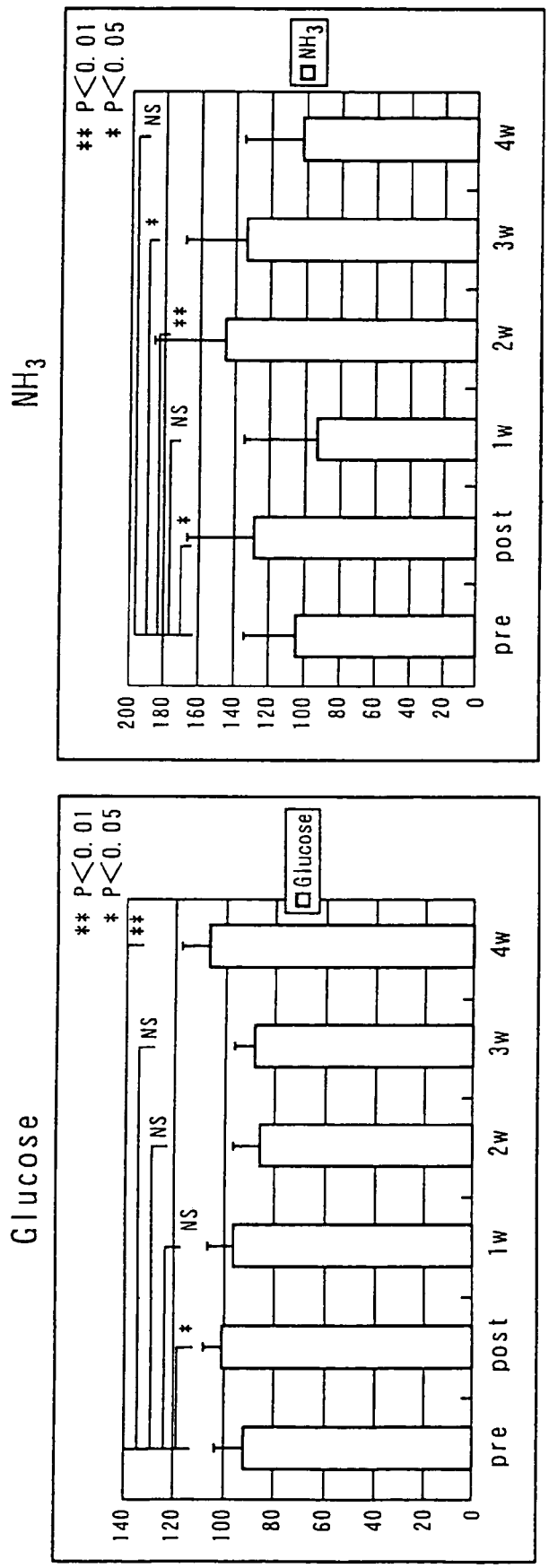
FIG. 17 shows the result of the experiment, representing in graphic form the glucose and $NH_3$ of the beagles used for the experiment.
Figure 19:
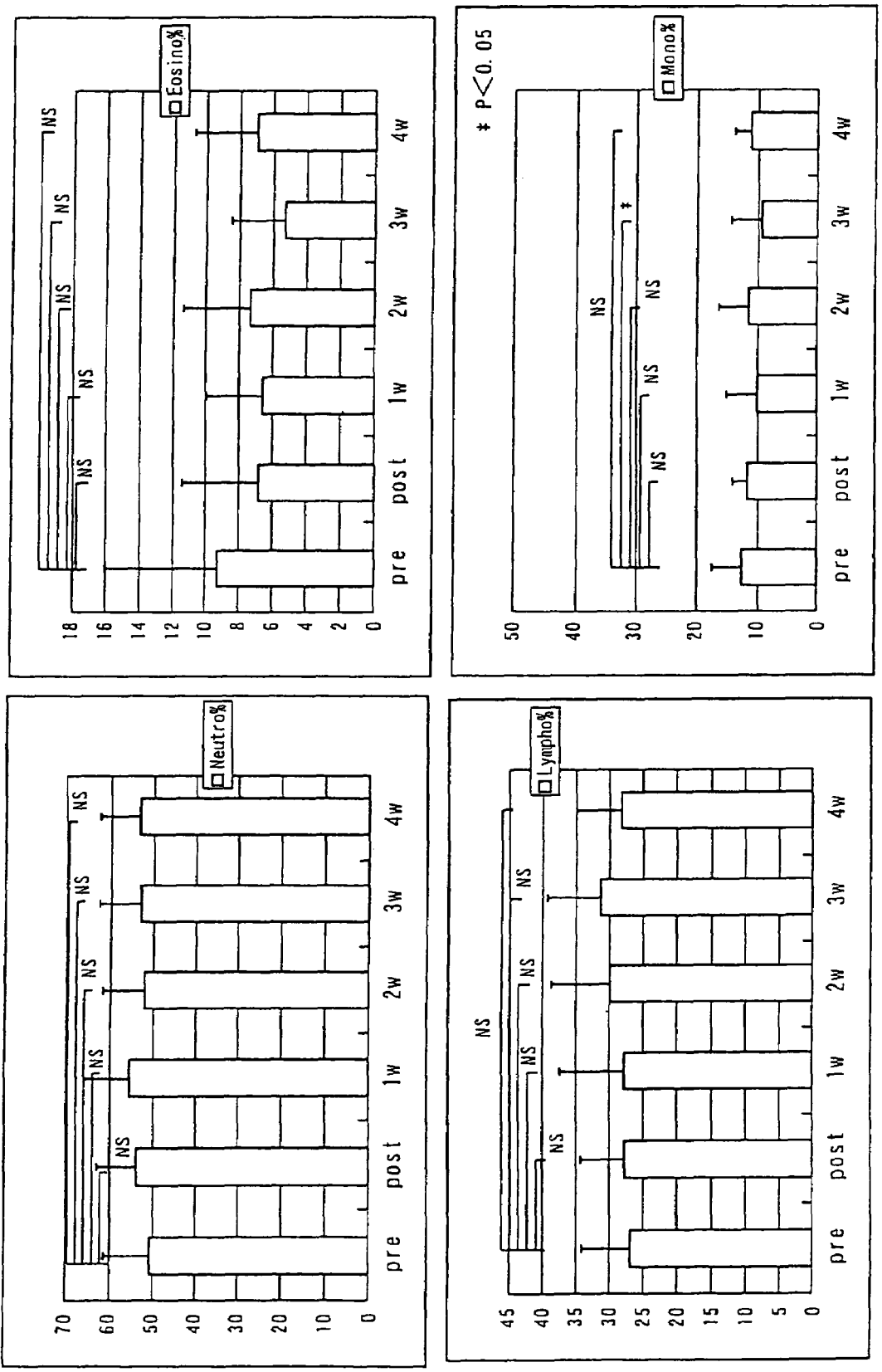
FIG. 19 shows the result of the experiment, representing in graphic form the fraction of white corpuscles of the beagles used for the experiment.

Body temperature, body weight, general physical condition . . . (see FIGS. 8 and 9)

Throughout the entire process, each of the experimental animals showed good physical conditions which remained unchanged from those before the experiment. Neither fever nor weight loss was observed.

(2) Blood Test

Tests on WBC, the fraction of white corpuscles, RBC, Hb, the number of blood platelets, TP, T-BiL, GOT, GPT, LDH, ALP, Amylase, CPK, Glucose, $NH_3$, BUN, Cr and the like were performed.

Results: (see FIG. 10, FIG. 11, FIG. 12, FIG. 13, FIG. 14, FIG. 15, FIG. 16, FIG. 17, FIG. 18 and FIG. 19)

A slight decrease in WBC was observed two weeks after the irradiation, but WBC recovered later. As for the fraction of white corpuscles, eosino decreased to 28% after the irradiation and after one week, and to 48% after three weeks, but recovered up to 72% after four weeks. As for RBC and Hb, a decrease of approximately 10% was observed for four weeks after the irradiation, but did not reach an abnormal value indicative of progressiveness.

Experiment 4: Variations of 8-OHdG (8-Hydroxydeoxyganosine) in Urine

By checking 8-OHdG which is a biomarker of oxidation damage to DNA, it is possible to know the degree of recovery of oxidation damage to DNA before and after microwave irradiation.

(1) Variations of 8-OHdG in Urine of Two Dogs Bearing Spontaneous Cancer

An operation method similar to Experiment 1 was performed for two days.

a) Kind: Yorkshire terrier, weight: 3.2 kg, castrated male, born in 1987, liver tumor, bladder stone, remarkable ascites.

b) Kind: Shih Tzu, weight: 4.3 kg, castrated female, born in 1985, mammary gland cancer, difficulty in gait.

Result: In a), the average value of 8-OHdG values of the original urine was 155, and the average value of 8-OHdG values in the urine after the irradiation was 42.5, and in b), the average value of 8-OHdG values of the original urine clearly decreased to 24, and the average value of 8-OHdG values in the urine after the irradiation also clearly decreased to 13.0.

Experiment 3: Variations of Living Cell (1) Variations of Living Cancer Cell

Method: Secretions which were sampled with cover glass after informed consent directly from carcinomatous tumor which appeared on a breast of a human body were observed under a 1000-power phase-contrast microscope, and a solid colony of cancer cells surrounded by cell membrane was found. After this sample was irradiated for 3 seconds with one microwave radiator apparatus, variations in form were observed on a time-lapse basis.

Figure 20:
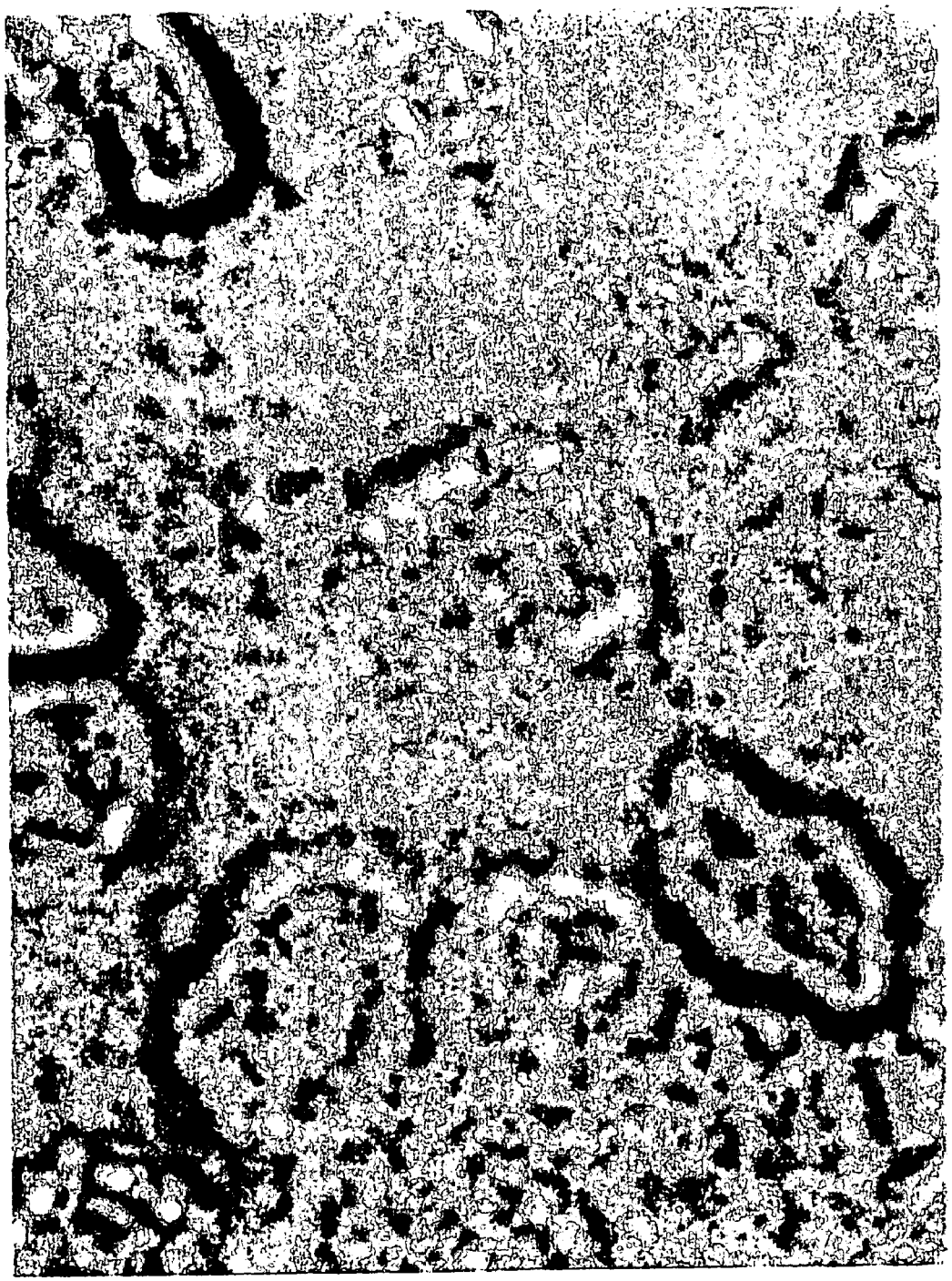
FIG. 20 is a microscopic photograph showing a variation period of the form of a sample which was left for 5 minutes after the sample was irradiated with microwaves from one microwave generator for 3 seconds from a distance of 30 cm.

Result: as shown in FIG. 20, after 5 seconds of microwave irradiation, the enlargement of cell membrane was found, and partial dissolution was found.

Figure 21:
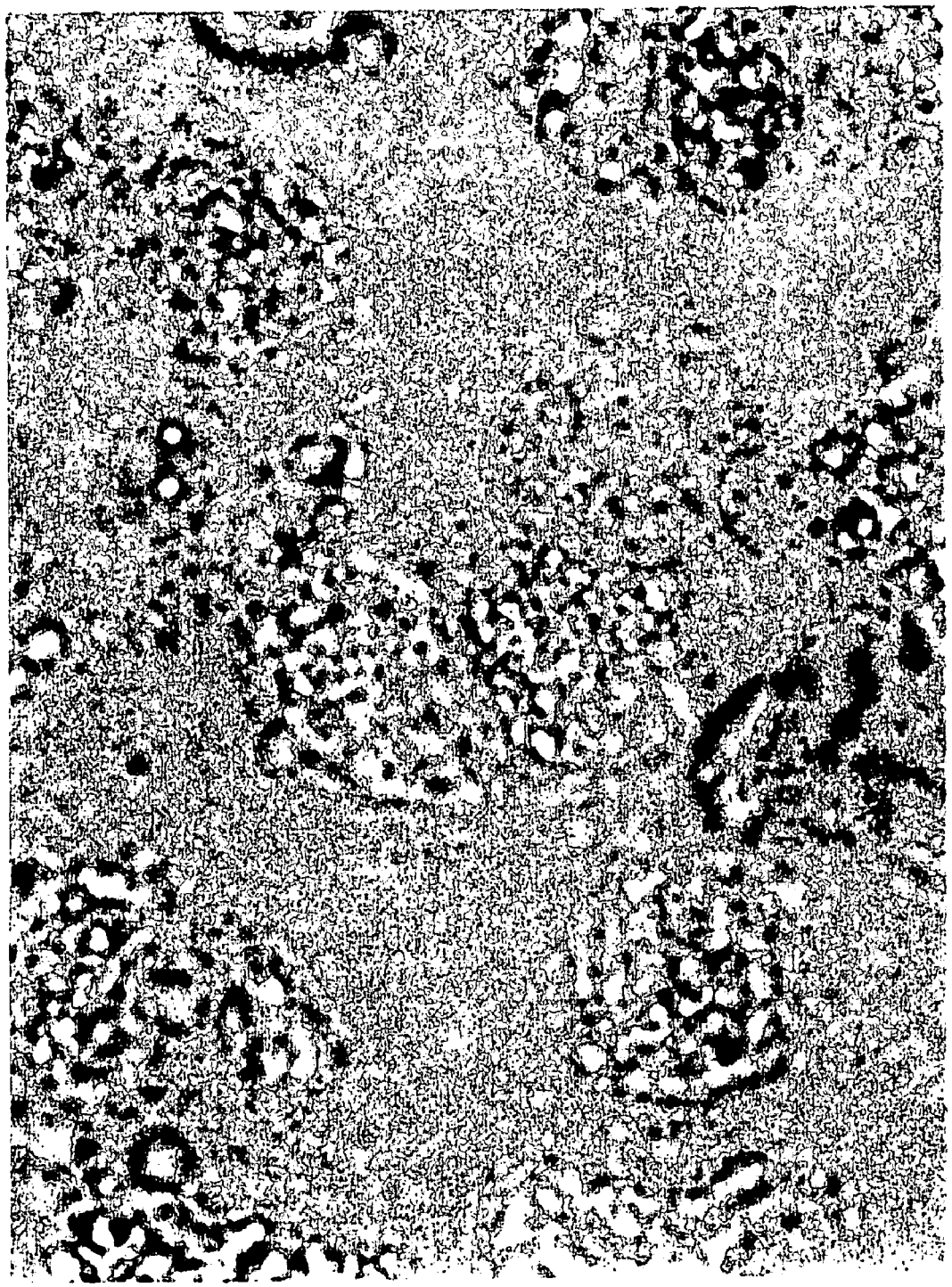
FIG. 21 is a microscopic photograph showing a variation of the form of the sample which was left for 30 minutes in the experiment shown in FIG. 20.

As shown in FIG. 21, after 30 minutes, the cell membrane was completely broken and disappeared, and the form of cytoplasm was lost.

No abnormality was found in the form of normal cells.

(2) Comparison with Normal Blood

Method: one drop of fresh blood sampled as a target from a fingertip of a normal person was, similarly to (1), irradiated for 3 seconds with one microwave radiator apparatus, and after that, variations in the forms of red corpuscles and white corpuscles were observed with a 1,000-power phase-difference microscope on a time-lapse basis.

Figure 22:
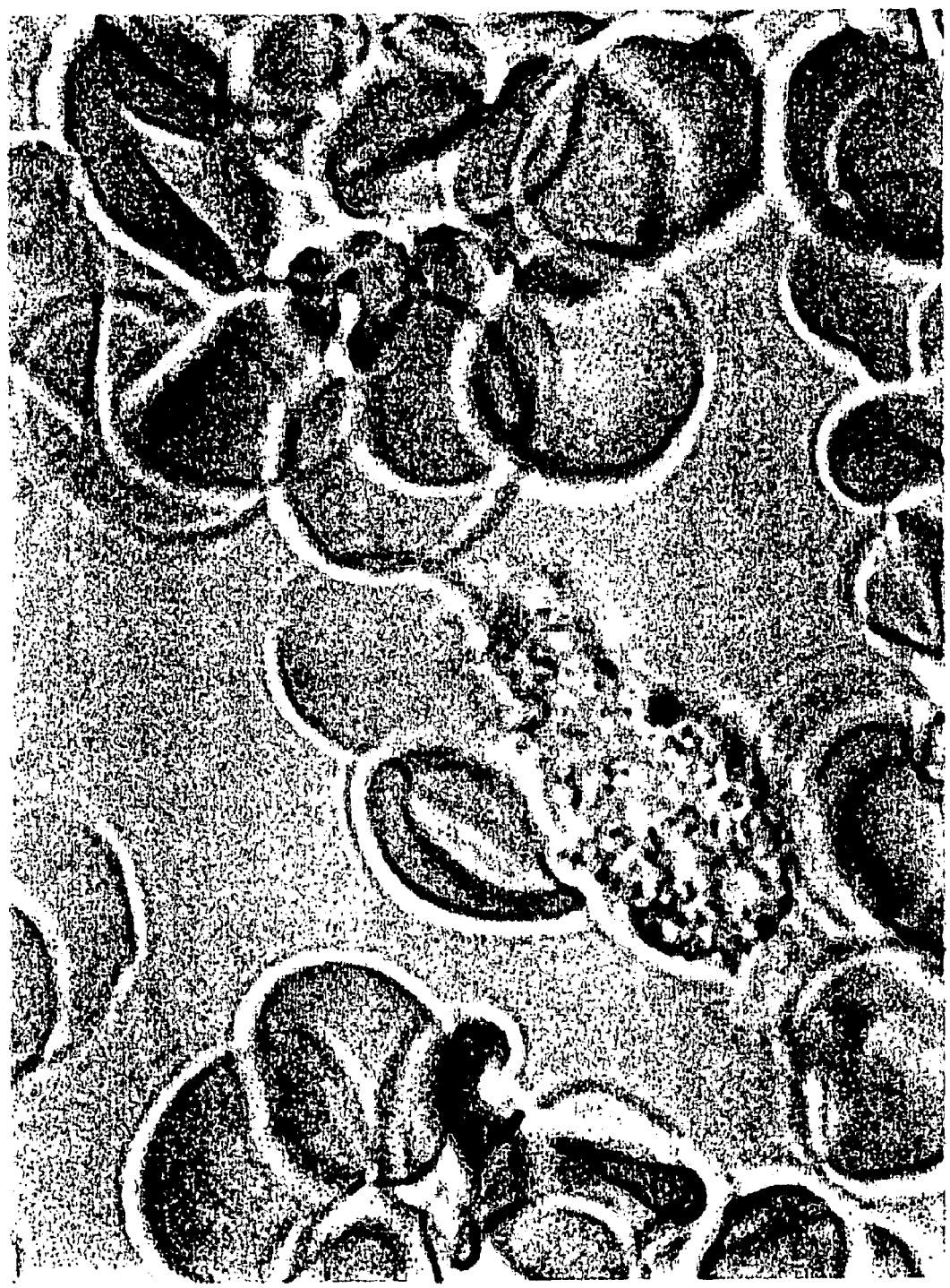
FIG. 22 is a microscopic photograph showing a variation of the form of a sample which was left for 5 minutes after one drop of blood sampled from a fingertip of a normal person was irradiated with microwaves from one microwave generator for 3 seconds from a distance of 30 cm.

Result: as shown in FIG. 22, no variations after the microwave irradiation were found, and white corpuscles after 30 minutes were migrating in rather brisk activity.

Discussion

In recent years, the concept of cancer treatment using microwaves-aims to generate heat by vibrating the molecules of water in a subject and coagulate cancer by means of the heat. In the current medical fields, an electrode is transdermally inserted into a liver to coagulate a liver cancer of diameter 2 cm or less, but there are disadvantages such as post-bleeding, the narrowness of an area which can be treated at a time and an increased number of treatment operations, so that radio waves are currently replacing microwaves. In addition, cancer treatment using microwaves is transurethrally applied to prostatomegaly and prostate cancer, but since irradiation time is 30 minutes or longer, an urethra and a rectum need to be cooled. As to liver cell carcinoma, Ming-de Lu, Jun-wei Chen et al. state that if the number of electrodes is increased to enhance the effect of treatment, the cancer treatment effectively works on even liver cell carcinoma of 6 cm or less (Radiology 2001 October; 221(1): 167–172). On the other hand, microwaves are finding a gradually wider range of applications such as irradiation onto bone cancer during operation and ablation of endometrorium. However, the current trend is to employ microwaves and radio waves in pinpoint treatment methods, with the result that the range of applications of those waves is naturally limited. In terms of cancer treatment, such a pinpoint treatment method is no better than symptomatic treatment.

The desirable conditions required to develop electromagnetic treatment are, among others, noninvasiveness, irradiation time reduced to minimize the influence of electromagnetic waves, and adoption of not related-art pinpoint irradiation but plane irradiation.

In this case, the range of applications of electromagnetic treatment is epoch-makingly enlarged. Accordingly, in our developed apparatus, since microwaves are simultaneously irradiated from a plane of over 20 cm$^2$, its effective area changes from point to plane so that the apparatus has higher power than the related art apparatus. In addition, two microwave radiator apparatus are oppositely disposed and simultaneously generate microwaves in units of several seconds, whereby a beat phenomenon occurs in the middle between the two and its power density reaches 1 W/cm$^2$. If a subject is placed there, free radicals which peculiarly exist in cancer repeat vibrations at high speeds owing to intense electromagnetic waves and generate heat before the temperature of body fluids abnormally rises, and only cancer cells can be selectively broken. This fact was proved from Experiments 2 and 3. In addition, since microwaves can be noninvasively irradiated from the outside of the body in units of several seconds, there is a merit which can minimize the influence of electromagnetic waves. If the apparatus is applied to clinical fields in the future, the apparatus effectively acts on, for example, lymph glands and unoperable wide-area cancers as well as tumor from the outside of the body in units of several seconds. Accordingly, the apparatus has the possibility that its range of applications can be remarkably expanded.

The influence of electromagnetic waves on living bodies becomes a problem. According to the experiment of Ivancica Trosic, the whole bodies of rats were irradiated with microwaves of 2,450 MHz at a power density set to 5–15 mW/cm$^2$ while the number of times of irradiation was being changed for 2 hours, and according to the result of observation, multinucleated giant cells were found. Trosic states that an increase in the number of nuclei in a cell depends on irradiation time and dosage (International Journal of Hygiene and Environmental Health 2001 November; 204 (2–3): 133–138). Accordingly, it is impossible to immediately determine that only this phenomenon represents a pathological symptom. It is natural that the influence of electromagnetic waves is determined by irradiation time and power density. Even in the case of a power density of 1W/cm$^2$, if the unit of irradiation time is several seconds, it can be presumed that the influence of electromagnetic waves on living bodies is within a negligible range. For example, even under strong ultraviolet rays, the influence of ultraviolet rays on living bodies can be neglected as long as irradiation time is short. However, there remains room for further research.

Bruce Hocking reports that some of workers who consistently handle microwaves show symptoms (microwave sickness) such as headache, sense of fatigue and autonomic imbalance (Occupational Medicine (Lond) 2001 February; 51(1): 66–69). These symptoms can be easily solved by preparing an aluminum wall with a ventilating portion formed therein.

As is apparent from the experiments using animals relative to the safety of the apparatus and the temporal variations of white corpuscles in living blood, excellent results were obtained. On the other hand, as to the effect of the apparatus on cancer, it has been found that cancer can be broken effectively and noninvasively in a short time under a new concept using free radicals surrounding a cancer.

INDUSTRIAL APPLICABILITY

In clinical test examples using the apparatus of the invention, the effect of treatment on cancer cells occurring in human bodies and animals is remarkably high, and side effects are not at all observed.

Bacteria and foci relative to cancer cells in the inside or the deep part of a body that is an affected part to be treated can be clinically completely removed by thermal energy. Incidentally, 42° C. or more is the best.

After informed consent, as clinical test examples, particularly patients suffering terminal serious cancers were treated as its clinical test example, and there were seen many examples that the resultant effect was manifested in one week, such patients showed signs of recovery and the pain of patients was successfully restrained. Of course, there were also examples in which patients were able to forget long-time pain without administration of morphine.

Furthermore, in examples of experiments using animals, abnormalities such as side effects were not at all found.

The invention claimed is:

1. A microelectromagnetic radiator apparatus comprising: microelectromagnetic radiators to be respectively disposed on opposite sides of a body in a mutually opposed manner each of said microelectromagnetic radiators including a magnetron for generating a wave and an electromagnetic wave horn each wave horn having an aperture with an adjustable opening degree for radiating said wave, wherein each of said microelectromagnetic radiators is constructed and arranged such that upon relative rotation between each of said microelectromagnetic radiators and the body, microelectromagnetic waves of 1.0–5 Ghz are generated by a corresponding magnetron and simultaneously radiated from a corresponding said wave horn for several seconds to cause the microelectromagnetic waves to reach a deep portion of the body.

2. The microelectromagnetic radiator apparatus according to claim 1, wherein said microelectromagnetic waves of 1.0–5 Ghz have an electromagnetic energy of approximately 500 W.

* * * * *